United States Patent
Kimmel et al.

(10) Patent No.: US 10,013,756 B2
(45) Date of Patent: Jul. 3, 2018

(54) METHODS AND SYSTEMS FOR MEASURING USE OF AN ASSISTIVE DEVICE FOR AMBULATION

(71) Applicant: Atlas5D, Inc., Cambridge, MA (US)

(72) Inventors: Zebadiah M. Kimmel, Cambridge, MA (US); Jonathan S. Varsanik, Brookline, MA (US)

(73) Assignee: Atlas5D, Inc., Cambridge, MA (US)

( * ) Notice: Subject to any disclaimer, the term of this patent is extended or adjusted under 35 U.S.C. 154(b) by 148 days.

(21) Appl. No.: 15/058,943

(22) Filed: Mar. 2, 2016

(65) Prior Publication Data

US 2016/0267652 A1    Sep. 15, 2016

Related U.S. Application Data

(60) Provisional application No. 62/132,883, filed on Mar. 13, 2015.

(51) Int. Cl.
  *G06K 9/00*  (2006.01)
  *G06T 7/00*  (2017.01)
  (Continued)

(52) U.S. Cl.
  CPC .......... *G06T 7/0012* (2013.01); *A61B 5/1114* (2013.01); *A61B 5/1128* (2013.01); *A61B 5/6887* (2013.01); *G06F 19/3418* (2013.01); *G06K 9/62* (2013.01); *G06N 7/005* (2013.01); *G06T 7/77* (2017.01); *A61B 5/0002* (2013.01);
  (Continued)

(58) Field of Classification Search
  None
  See application file for complete search history.

(56) References Cited

U.S. PATENT DOCUMENTS

| | | | |
|---|---|---|---|
| 4,406,544 A | 9/1983 | Takada et al. | |
| 4,650,330 A | 3/1987 | Fujita | |

(Continued)

FOREIGN PATENT DOCUMENTS

| | | |
|---|---|---|
| WO | WO-01/001354 A1 | 1/2001 |
| WO | WO-2013/058985 A1 | 4/2013 |
| WO | WO-2014/112632 A1 | 7/2014 |

OTHER PUBLICATIONS

Ergotron Dock Locker, dated Feb. 6, 2015, <http://www.hpi.com/ergotron-dock-locker-secure-table-stand.html> retrieved from google on Jan. 6, 2017.

(Continued)

*Primary Examiner* — Nirav G Patel
(74) *Attorney, Agent, or Firm* — Choate, Hall & Stewart LLP; William R. Haulbrook

(57) ABSTRACT

The disclosed technology relates generally to systems for measuring the frequency and duration of an individual's use of an assistive device for mobility, such as a cane, in day-to-day life at home. In certain embodiments, the system is a stand-alone unit that does not require the monitored individual to wear any special sensors or use any special assistive devices. Further, in certain embodiments, the system does not require the use of visual-light images or video. The systems and methods, in certain embodiments, gather day-to-day metrics of frequency and duration of assistive-device use and may be used to monitor changes over time of the use of an assistive device by an individual for ambulation.

20 Claims, 2 Drawing Sheets

(51) Int. Cl.
*A61B 5/00* (2006.01)
*A61B 5/11* (2006.01)
*G06F 19/00* (2018.01)
*G06K 9/62* (2006.01)
*G06N 7/00* (2006.01)
*G06T 7/77* (2017.01)
*G06F 17/30* (2006.01)

(52) U.S. Cl.
CPC ......... *A61B 5/1124* (2013.01); *A61B 2503/08* (2013.01); *A61B 2505/07* (2013.01); *G06F 17/30259* (2013.01); *G06T 2207/10021* (2013.01); *G06T 2207/10028* (2013.01); *G06T 2207/10048* (2013.01); *G06T 2207/20076* (2013.01); *G06T 2207/30196* (2013.01)

(56) References Cited

U.S. PATENT DOCUMENTS

| | | |
|---|---|---|
| 5,530,652 A | 6/1996 | Croyle et al. |
| 5,742,521 A | 4/1998 | Ellenby et al. |
| 6,111,755 A | 8/2000 | Park |
| 7,440,590 B1 | 10/2008 | Hassebrook et al. |
| 7,551,432 B1 | 6/2009 | Bockheim et al. |
| 7,684,185 B2 | 3/2010 | Farrugia |
| 8,269,834 B2 | 9/2012 | Albertson et al. |
| 8,613,666 B2 | 12/2013 | Esaki et al. |
| 8,639,020 B1 | 1/2014 | Kutliroff et al. |
| 8,775,710 B1 | 7/2014 | Miller et al. |
| 8,787,663 B2 | 7/2014 | Litvak et al. |
| 8,902,607 B1 | 12/2014 | Chang et al. |
| 9,037,354 B2 | 5/2015 | Mondragon et al. |
| 9,189,886 B2 | 11/2015 | Black et al. |
| 9,341,464 B2 | 5/2016 | Kimmel |
| 9,361,696 B2 | 6/2016 | Allezard et al. |
| 9,393,695 B2 | 7/2016 | Scott et al. |
| 9,513,667 B2 | 12/2016 | Pais et al. |
| 9,520,072 B2 | 12/2016 | Sun et al. |
| 9,524,554 B2 | 12/2016 | Plagge et al. |
| 2001/0001354 A1 | 5/2001 | Peter-Hoblyn et al. |
| 2003/0076414 A1 | 4/2003 | Sato et al. |
| 2003/0209893 A1 | 11/2003 | Breed et al. |
| 2003/0231788 A1 | 12/2003 | Yukhin et al. |
| 2004/0083142 A1 | 4/2004 | Kozzinn |
| 2004/0104905 A1 | 6/2004 | Chung et al. |
| 2004/0236456 A1 | 11/2004 | Pieper et al. |
| 2005/0094879 A1 | 5/2005 | Harville |
| 2005/0162824 A1 | 7/2005 | Thompson |
| 2006/0252541 A1 | 11/2006 | Zalewski et al. |
| 2007/0229850 A1 | 10/2007 | Herber |
| 2007/0252831 A1 | 11/2007 | Lind et al. |
| 2008/0103637 A1 | 5/2008 | Bliven et al. |
| 2009/0244309 A1 | 10/2009 | Maison et al. |
| 2010/0007717 A1 | 1/2010 | Spektor et al. |
| 2010/0049095 A1 | 2/2010 | Bunn et al. |
| 2010/0172567 A1 | 7/2010 | Prokoski |
| 2010/0191541 A1 | 7/2010 | Prokoski |
| 2010/0226533 A1 | 9/2010 | Bharath et al. |
| 2011/0052006 A1 | 3/2011 | Gurman et al. |
| 2011/0193939 A1 | 8/2011 | Vassigh et al. |
| 2011/0205337 A1 | 8/2011 | Ganapathi et al. |
| 2011/0206273 A1 | 8/2011 | Plagemann et al. |
| 2011/0211044 A1 | 9/2011 | Shpunt et al. |
| 2011/0211754 A1 | 9/2011 | Litvak et al. |
| 2011/0288964 A1 | 11/2011 | Linder et al. |
| 2011/0298801 A1 | 12/2011 | Wexler et al. |
| 2012/0046101 A1 | 2/2012 | Marks et al. |
| 2012/0076361 A1 | 3/2012 | Fujiyoshi |
| 2012/0120580 A1 | 5/2012 | Yukawa et al. |
| 2012/0128327 A1 | 5/2012 | Matsubara |
| 2012/0159290 A1 | 6/2012 | Pulsipher et al. |
| 2012/0162483 A1 | 6/2012 | Sutton et al. |
| 2012/0229634 A1 | 9/2012 | Laett et al. |
| 2012/0242501 A1 | 9/2012 | Tran et al. |
| 2012/0257814 A1 | 10/2012 | Kohli et al. |
| 2012/0269384 A1 | 10/2012 | Jones et al. |
| 2012/0326959 A1 | 12/2012 | Murthi et al. |
| 2013/0048722 A1 | 2/2013 | Davis et al. |
| 2013/0109253 A1 | 5/2013 | Gammon et al. |
| 2013/0163170 A1 | 6/2013 | Chen |
| 2013/0163879 A1 | 6/2013 | Katz et al. |
| 2013/0315475 A1 | 11/2013 | Song et al. |
| 2013/0335235 A1 | 12/2013 | Carr et al. |
| 2014/0163330 A1 | 6/2014 | Horseman |
| 2014/0243686 A1 | 8/2014 | Kimmel |
| 2014/0279740 A1 | 9/2014 | Wernevi et al. |
| 2014/0298379 A1 | 10/2014 | Singh |
| 2014/0299775 A1 | 10/2014 | Kimmel |
| 2014/0300907 A1 | 10/2014 | Kimmel |
| 2014/0376172 A1 | 12/2014 | Love et al. |
| 2015/0000025 A1 | 1/2015 | Clements |
| 2015/0213702 A1 | 7/2015 | Kimmel |
| 2015/0325004 A1 | 11/2015 | Utsunomiya et al. |
| 2015/0331463 A1 | 11/2015 | Obie et al. |
| 2016/0127664 A1* | 5/2016 | Bruder ................. G01S 7/4816 463/30 |
| 2016/0231778 A1 | 8/2016 | Kaneko |
| 2016/0247017 A1 | 8/2016 | Sareen et al. |
| 2016/0266607 A1 | 9/2016 | Varsanik et al. |
| 2016/0307382 A1* | 10/2016 | Herman ............ G07C 9/00158 |
| 2016/0331277 A1 | 11/2016 | Kimmel |

OTHER PUBLICATIONS

Loker et al., "Size-specific Analysis of Body Scan Data to Improve Apparel Fit," Journal of Textile and Apparel, Technology and Management, 4(3): 4-6 (2005).

Stone. E.E. and Skubic, M., Evaluation of an Inexpensive Depth Camera for Passive In-Home Fall Risk Assessment, 2011 5th International Conference on Pervasive Computing Technologies for Healthcare (PervasiveHealth) and Workshops, pp. 71-77 (2011).

Viktor et al., "Measuring to Fit: Virtual Tailoring through Cluster Analysis and Classification," NRC Publications Archive, entire document (2006).

\* cited by examiner

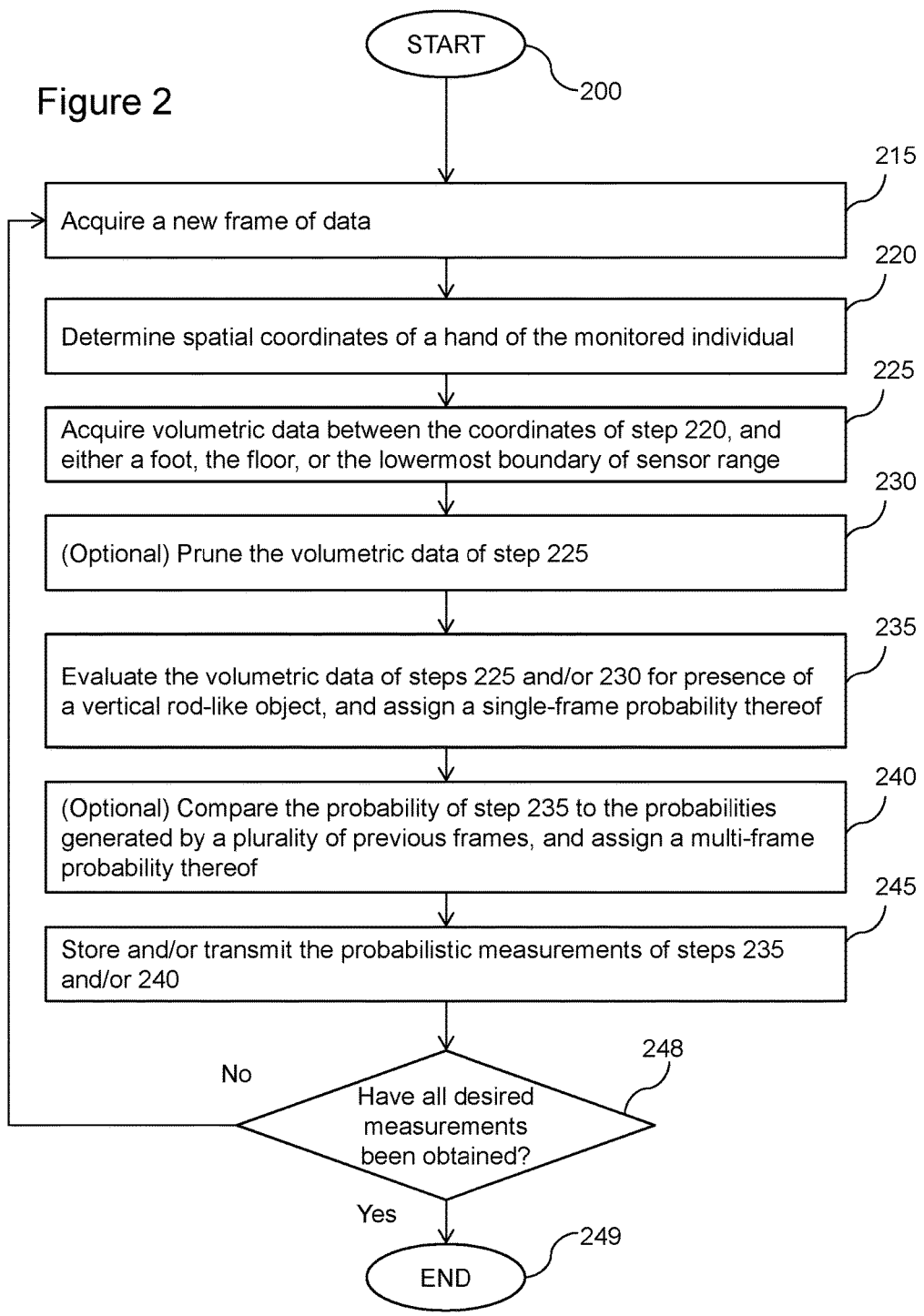

METHODS AND SYSTEMS FOR MEASURING USE OF AN ASSISTIVE DEVICE FOR AMBULATION

RELATED APPLICATIONS

This application claims priority to and the benefit of U.S. Provisional Patent Application No. 62/132,883, filed Mar. 13, 2015, entitled "Methods and Systems for Measuring Use of an Assistive Device for Ambulation," the content of which is incorporated by reference herein in its entirety.

This application relates to U.S. Provisional patent application Ser. No. 15/058,665, filed Mar. 2, 2015, entitled "System for Integrating Commercial Off-The-Shelf Devices to Produce a Modular Interaction Platform" and PCT Application No. PCT/US/2012/058534, filed Oct. 3, 2012, entitled "Method and Apparatus for Detecting Deterioration of Health Status," the contents of each of which are incorporated herein in their entireties.

FIELD OF THE INVENTION

The disclosed technology relates generally to methods and systems for monitoring an individual. More particularly, in certain embodiments, the invention relates to automatic detection of whether an individual is using an assistive device, such as a cane, crutch, rollator, or mobility walker, for walking.

BACKGROUND OF THE INVENTION

Human motion can be impaired by a wide variety of diseases that affect nerve, muscle, bone, or blood vessels, such as multiple sclerosis, traumatic brain injury, stroke, osteoarthritis, and diabetes, among others. Typically, an individual's motion is increasingly impaired as the disease becomes more severe. Walking is especially susceptible to impairment, as the nerves and blood vessels to the legs and feet are vulnerable to damage. Further, because walking requires tremendous energy expenditure and complex coordination between multiple body systems.

When motion becomes sufficiently impaired, an individual employs an assistive device to ease (or to enable at all) ambulation. Typically, the frequency and duration at which an assistive device is used depends on the severity of the disease. For example, when the pain of osteoarthritis increases, or when the imbalance of multiple sclerosis exacerbates, the individual increases use of a cane or crutch; and when the disease ebbs again, the individual reduces usage.

The degree to which an individual uses an assistive device in daily life would be clinically valuable, so as to track the severity and course of a disease, and to assess how an individual is responding to treatment over time. However, measuring the frequency or the duration at which an individual uses an assistive device in their home is extremely difficult. Surveys or questionnaires rely on memory and active participation, which require a lot of effort and are not very reliable. Canes or crutches with embedded sensors are bulky, expensive, run out of power, and provide only low-quality, high-noise data. Thus, there is a need for a system that can measure the frequency and duration of use of an assistive device for mobility, such as a cane, without any special requirement for worn devices or special canes, in order to enable monitoring of the health status of an individual who relies on such assistive devices.

SUMMARY OF THE INVENTION

The disclosed technology relates generally to systems for measuring the frequency and duration of an individual's use of an assistive device, such as a cane, for mobility in day-to-day life at home. The disclosed technology does not require any special effort on the part of the individual being monitored—in particular, there are no special devices to wear or special canes to buy—and will safeguard the individual's privacy.

The disclosed technology measures usage of an assistive device by an individual, without modification of the assistive device, thereby giving the monitored individual the freedom to select any assistive device that is desired. Further, the disclosed technology does not require any special sensors to be worn by the monitored individual. The disclosed technology, in certain embodiments, does not require the use of images or video, thereby safeguarding the monitored individual's privacy.

The disclosed technology, in certain embodiments, utilizes a 3D depth sensor to capture a depth map of an area (e.g., the field of view of the depth camera and/or a room or a portion of a room). The data from the sensor is sent to a computational device, such as a tablet computer, mobile phone, or laptop, where a software module transmits measurements from the computational device to storage (e.g., remote storage, such as one or more remote servers). In some implementations, the software module operates the 3D depth sensor. The software module on the computational device performs some, all, or none of the computation described herein to determine whether an individual is using an assistive device. In some embodiments, the 3D depth sensor operates in the infrared spectrum. In some embodiments, no visual-light photos or video of the subject are acquired.

The disclosed technology, in certain embodiments, includes a method of detecting an individual's use an assistive device for mobility such that a severity of a disease and/or an individual's response to a treatment can be tracked/assessed over time. In certain embodiments, the method includes capturing, by a depth sensor (e.g., a 3D depth sensor), a time sequence of frames of depth data for a space (e.g., a space at least occasionally inhabited by the individual), wherein the time sequence of frames includes a plurality of frames; determining, by the processor of a computing device, spatial coordinates of a hand of the individual in each frame in the sequence of frames; determining, by the processor, volumetric data beneath the hand of the individual in each frame of the sequence of frames; and determining, by the processor, a plurality of probabilities of whether the individual is holding the assistive device, wherein each probability of the plurality of probabilities is a probability, for a frame of the sequence of frames, that the hand of the individual is holding an object in space consistent with the shape, size, and orientation of an assistive device for ambulation based at least in part on the volumetric data beneath the hand of the individual in the frame.

In certain embodiments, the method includes, prior to determining a plurality of probabilities, pruning of the volumetric data (e.g., eliminating volumetric data associated with pixels in the depth map that appear to be erroneous or for which no depth value was successfully calculated).

In certain embodiments, the method includes determining, by the processor, a multi-frame probability that the hand of the individual is holding an object in space consistent with the shape, size, and orientation of an assistive device for ambulation based at least in part by comparing (e.g., averaging) the plurality of probabilities for the sequence of frames.

In certain embodiments, the method includes providing, by an energy emitter (e.g., infrared light emitter), energy within a field-of-view for generating a depth map of the field-of-view. In certain embodiments, the depth sensor is positioned (i) at a height within a predetermined range of acceptable vertical heights and (ii) at an angular orientation within a predetermined range of acceptable angular orientations.

In certain embodiments, the method includes determining, by the processor, a probability for a portion of the time sequence of frames that the individual is using an assistive device for ambulation over the duration of time encompassed by the portion of the sequence of frames, wherein the portions of the time sequence of frames includes two or more frames.

In certain embodiments, the method includes storing in a database, by the processor, the plurality of probabilities such that frequencies and durations of assistive-device use are stored for the individual. In certain embodiments, the method includes storing in a database (e.g., the database of claim 7), by the processor, at least one of the plurality of probabilities such that historic measurements are stored for the individual. In certain embodiments, at least a portion of the data stored in the database is accessible via an online portal such that the historic measurements (e.g., at least one of the plurality of probabilities) for the individual are viewable.

In certain embodiments, the assistive device is a cane, crutch, rollator, or mobility walker. In certain embodiments, the depth sensor does not employ visible light to acquire depth data. In certain embodiments, a health status of the individual is monitored without acquiring visual-light images or video. In certain embodiments, each probability of the plurality of probabilities is determined based at least in part on the of one or more of a spatial band-pass filter, curve-fitting algorithm corresponding to a 3D hemispherical shape, 3D edge-detection, and vertical linear Hough transform filter.

In certain embodiments, the method includes capturing, by an audio sensor (e.g., microphone; e.g., an audio sensor on the computing device), sound data for determining the decline in the health status of the individual. In certain embodiments, the data captured corresponding to the individual within the field-of-view is captured in real-time while the individual moves about in real-time.

In certain embodiments, energy emitted by an energy emitter (e.g., the energy emitter of claim 2) includes a pattern of emitted energy, energy detected by the depth sensor includes a pattern of reflected energy, and the depth data for the field-of-view is generated based a difference between the pattern of the emitted energy and the pattern of reflected energy.

In certain embodiments, the depth data for the field-of-view is generated based a difference between a phase of emitted energy and a phase of captured energy.

In certain embodiments, In certain embodiments, the method includes, prior to determining spatial coordinates of the hand of the individual in each frame in the sequence of frames, extracting, by the processor, skeleton data for each frame in the sequence of frames, wherein the spatial coordinates of the hand of the individual in each frame in the time sequence of frames are determined based at least in part on the skeleton data for the respective frame.

The disclosed technology, in certain embodiments, includes a system of detecting an individual's use an assistive device for mobility such that a severity of a disease and/or an individual's response to a treatment can be tracked/assessed over time. In certain embodiments, the system includes at least one energy emitter (e.g., infrared light emitter) for emitting energy within a field of view for generating a depth map of the field-of-view; at least one depth sensor for capturing energy reflected from one or more objects positioned within the field of view, wherein the one or more objects includes the individual; and a computing device including a processor and a memory storing instructions thereon, that when executed by the processor, cause the processor to: determine spatial coordinates of the hand of the individual in each frame in the sequence of frames; determine volumetric data beneath the hand of the individual in each frame of the sequence of frames; and determine a plurality of probabilities of whether the individual is holding the assistive device, wherein each probability of the plurality of probabilities is a probability, for a frame of the sequence of frames, that the hand of the individual is holding an object in space consistent with the shape, size, and orientation of an assistive device for ambulation based at least in part on the volumetric data beneath the hand of the individual in the frame.

In certain embodiments, the system the instructions stored on the memory include instructions that, when executed by the processor, cause the processor to: prior to determining a plurality of probabilities, prune the volumetric data (e.g., eliminate volumetric data associated with pixels in the depth map that appear to be erroneous or for which no depth value was successfully calculated).

In certain embodiments, the instructions stored on the memory include instructions that, when executed by the processor, cause the processor to: determine a multi-frame probability that the hand of the individual is holding an object in space consistent with the shape, size, and orientation of an assistive device for ambulation based at least in part by comparing (e.g., averaging) the plurality of probabilities for the sequence of frames.

In certain embodiments, the depth sensor is positioned (i) at a height within a predetermined range of acceptable vertical heights and (ii) at an angular orientation within a predetermined range of acceptable angular orientations.

In certain embodiments, the instructions stored on the memory include instructions that, when executed by the processor, cause the processor to: determine a probability for a portion of the time sequence of frames that the individual is using an assistive device for ambulation over the duration of time encompassed by the portion of the sequence of frames, wherein the portions of the time sequence of frames includes two or more frames.

In certain embodiments, the instructions stored on the memory include instructions that, when executed by the processor, cause the processor to: store the plurality of probabilities in a database such that frequencies and durations of assistive-device use are stored for the individual.

In certain embodiments, the instructions stored on the memory include instructions that, when executed by the processor, cause the processor to: store at least one of the plurality of probabilities in a database such that historic measurements are stored for the individual. In certain embodiments, at least a portion of the data stored in the database is accessible via an online portal such that the historic measurements (e.g., at least one of the plurality of probabilities) for the individual are viewable.

In certain embodiments, the assistive device is a cane, crutch, rollator, or mobility walker. In certain embodiments, the depth sensor does not employ visible light to acquire depth data. In certain embodiments, a health status of the individual is monitored without acquiring visual-light images or video.

In certain embodiments, each probability of the plurality of probabilities is determined based at least in part on the of one or more of a spatial band-pass filter, curve-fitting algorithm corresponding to a 3D hemispherical shape, 3D edge-detection, and vertical linear Hough transform filter.

In certain embodiments, an audio sensor (e.g., microphone; e.g., an audio sensor on the computing device) for capturing sound data for determining the decline in the health status of the individual. In certain embodiments, the data captured corresponding to the individual within the field-of-view is captured in real-time while the individual moves about in real-time.

In certain embodiments, energy emitted by the at least one energy emitter includes a pattern of emitted energy, energy detected by the at least one depth sensor includes a pattern of reflected energy, and the depth data for the field-of-view is generated based a difference between the pattern of the emitted energy and the pattern of reflected energy.

In certain embodiments, the depth data for the field-of-view is generated based a difference between a phase of emitted energy and a phase of captured energy.

In certain embodiments, the instructions stored on the memory include instructions that, when executed by the processor, cause the processor to: prior to determining spatial coordinates of the hand of the individual in each frame in the sequence of frames, extract skeleton data for each frame in the sequence of frames, wherein the spatial coordinates of the hand of the individual in each frame in the time sequence of frames are determined based at least in part on the skeleton data for the respective frame.

BRIEF DESCRIPTION OF DRAWINGS

The foregoing and other objects, aspects, features, and advantages of the present disclosure will become more apparent and better understood by referring to the following description taken in conjunction with the accompanying drawings, in which:

FIG. 2 is a block diagram of an example software module to drive the depth sensor and the tablet computer, according to a specific embodiment of the present disclosure.

Figure 1:
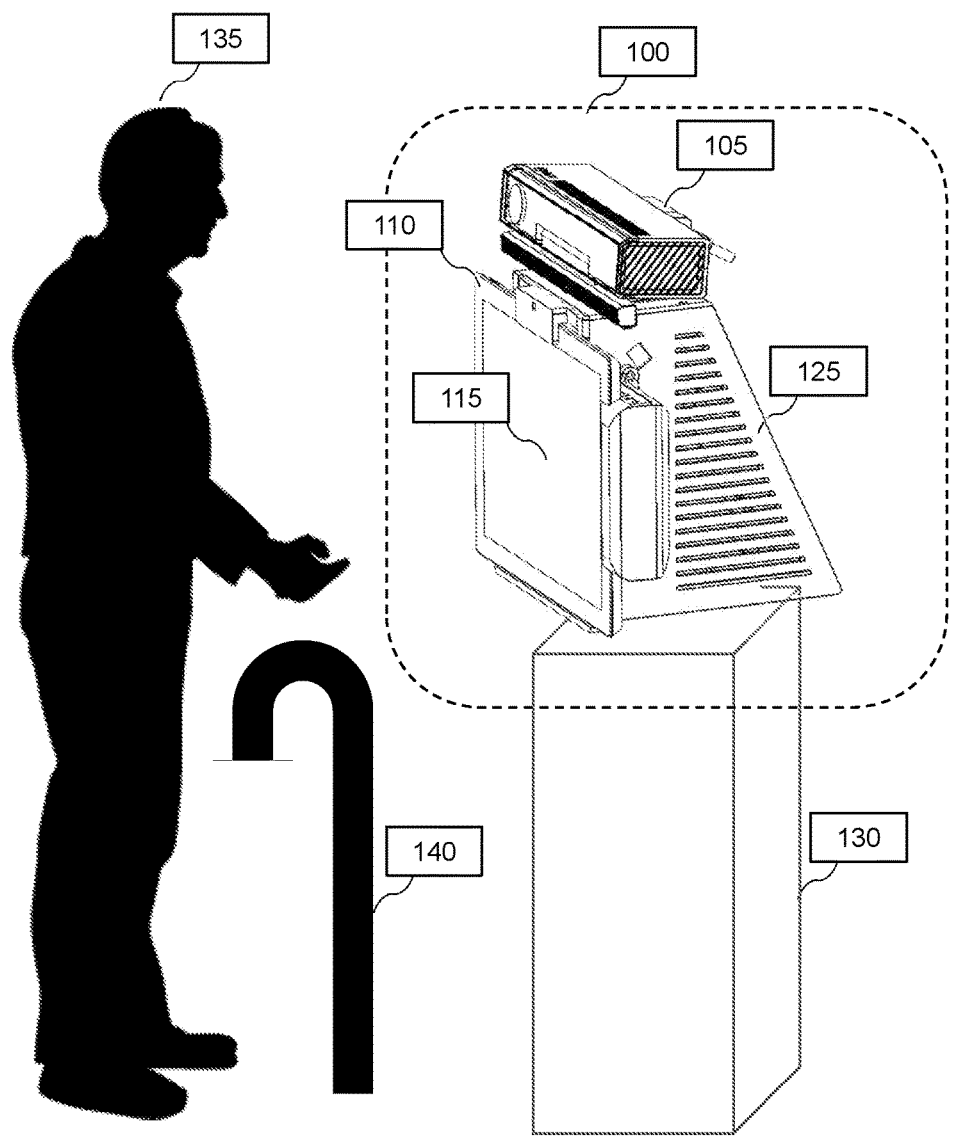
FIG. 1 is an illustration of an example of the hardware of a system integrating a depth sensor and a tablet computer, according to an embodiment of the present disclosure.

The features and advantages of the present disclosure will become more apparent from the detailed description set forth below when taken in conjunction with the drawings, in which like reference characters identify corresponding elements throughout. In the drawings, like reference numbers generally indicate identical, functionally similar, and/or structurally similar elements.

DETAILED DESCRIPTION OF THE INVENTION

The present disclosure describes methods and systems to measure the frequency and duration of use of an assistive device, such as a cane, for mobility, thereby allowing the severity and course of a disease to be tracked and/or an individual's response to a treatment to be assessed over time. The disclosed technology accomplishes this without requiring the monitored individual to modify their assistive device or wear any special sensors. The system, in some implementations, utilizes a depth-camera sensor (e.g., a 3D sensor or camera), computation system (e.g., tablet or mobile phone), communications system, and power system.

Kimmel describes using 3D sensors and processing equipment to perform health monitoring in the home in International Application No. PCT/US12/058534, filed Oct. 3, 2012, entitled Method and Apparatus for Detecting Deterioration of Health Status. Existing health-monitoring systems center on tracking the movement or behavior of a human being, and so they lack the capability to measure the employment of an nonhuman, inanimate assistive device for mobility. The ability to track canes, crutches, etc., is especially valuable in applications that involve monitoring the health status of an individual as described in International Application No. PCT/US12/058534. An enclosure that is especially-well-suited to deploy an assistive-device-tracking system using COTS (commercial-off-the-shelf) hardware is described by Varsanik in 62/131,568.

For example, depth data may be calculated based on a "time-of-flight" method. In this method, light with known physical characteristics (such as wavelength) is emitted into a field-of-view. An energy sensor, such as a camera, receives the light that is reflected from the field-of-view. Changes in the physical characteristics of the light between its being emitted and its being received—for example, the round-trip transit time of a light pulse, or the phase shift of an emitted waveform allow calculation of the distance to various objects (that reflect the light) in the field-of-view. If light pulses are utilized (for example, to measure round-trip transit time), the emitter can be, for example, a pulsed LED. If continuous light is utilized (for example, to measure phase shift), the emitter can be, for example, a laser. Time-of-flight cameras are a subset of LIDAR (Light Detection and Ranging) technologies, in which emitted-and-reflected light is used to remotely gauge the distance or other properties of a target. LIDAR cameras are similar to radar devices; the main difference is that radar bounces radio waves off target objects, but LIDAR uses ultraviolet, visible, or near-infrared light. Mesa Imaging AG, of Zurich, Switzerland, is an example of a company that manufactures devices to acquire depth data through time-of-flight: for example, its SR4000 time-of-flight camera.

Besides LIDAR, a different method of calculating depth data is through the use of "pattern deformation methods," also sometimes called "light coding". In pattern deformation methods, a light pattern with known physical characteristics (such as pattern shape and spacing) is emitted into a field-of-view. An energy sensor, such as a camera, receives the light pattern that is reflected from the field-of-view. Changes in the pattern between its being emitted and its being received—for example, gridlines moving closer further apart, or average distances between speckled dots growing or shrinking—allow calculation of the distance to various objects (that reflect the light) in the field-of-view.

In contrast to time-of-flight or LIDAR, the specific wavelengths or transit times of the emitted light are not crucial; what matters in pattern-deformation methods are the emitted pattern in which the light is placed, and how that emitted pattern is subsequently reflected and deformed by objects in the field-of-view. Because the specific wavelength is less important in pattern-deformation methods, a common choice of wavelength in such methods is infrared, which light cannot be seen by the human eye, and can be superimposed on a scene without disturbing people. If the light pattern is relatively fixed and constant, it is called "structured light"—often, structured-light patterns are grids of regular lines.

If the light pattern exhibits random or pseudorandom variation, it is called "coded light"—often, coded-light patterns are lattices of dots. (The reason why random or pseudorandom variations may be used in light patterns is so that small areas of the pattern will "look slightly different" compared to each other, enabling easier lining-up and registration of the emitted and reflected patterns.) PrimeSense Limited, of Tel Aviv, Israel, is an example of a company that manufactures sensors to acquire depth data through pattern deformation: its sensors are embedded in, for example, the Microsoft Kinect device (Microsoft Corp., Seattle, USA) and the Asus Xtion device (Asustek Computer Inc., Taipei, Taiwan).

Besides time-of-flight, LIDAR, and pattern deformation, a different method of acquiring depth data is through the use of emitted energy that is not light. For example, sound (rather than light) may be emitted and bounced off objects; the reflected physical characteristics of the sound, such as round-trip transit time, or frequency or phase shift, may be used to calculate depth or other characteristics of the objects in the field-of-view. Sommer Mess-Systemtechnik, of Koblach, Austria is an example of a company that manufactures devices to acquire depth data through ultrasonic impulses: for example, its USH-8 sensor, which uses ultrasonic impulses to measure snow depth.

FIG. 1 illustrates an implementation of an example system 100 integrating a depth sensor 105 and a tablet computer 110. The tablet computer 110 executes software module 115. The hardware components, for example, may be packaged inside an enclosure 125 or placed upon a table or shelf 130. The system monitors a field-of-view, such a room or a portion of a room. In the example shown in FIG. 1, an individual 135 is present in the room and is using an assistive device 140 (such as a cane). The disclosed system 100 determines whether the individual 135 is using the assistive device 140, thereby allowing the severity and course of a disease to be tracked and/or an individual's response to a treatment to be assessed over time.

FIG. 2 illustrates a block diagram of an example of software module 115. The software module 115 begins at step 200.

In step 215, a new frame of data is acquired from the depth sensor (e.g., depth sensor 105). "Frame" as used herein refers to a collection of depth data describing the distances to objects in the field-of-view, all at substantially the same moment in time. A frame of data may, in addition to depth data, also contain skeleton data which identifies the locations of a human's joints (such as heads or hands) in 3D space. A frame of data may, in addition to depth data, also contain pixel label data which labels pixels corresponding to the body surfaces of humans in the field-of-view. A detailed description of these data types is described in International Application No. PCT/US/2012/058534. To help protect the privacy of the monitored individual, all of the data types acquired in step 215 may not require visible light.

In step 220, the spatial coordinates (e.g., the x, y, and z coordinates relative to depth sensor 105 in millimeters) of a hand of the monitored individual are determined. Such coordinates may be provided in the "skeleton data" of step 215. Examples of commercially-available depth sensors 105 that can provide "skeleton data" with hand coordinates include the Microsoft Kinect by Microsoft Corporation of Redmond, Wash., the Softkinetic DepthSense by Softkinetic International of Brussels, Belgium, the Structure Sensor by Occipital of San Francisco, Calif., and the Argos 3D by Bluetechnix Group GmbH of Vienna, Austria.

In step 225, the volumetric data (i.e., depth data) from step 215 is cropped so as to preserve at least a volume of spatial data between the hand coordinates of step 220, and a lowermost boundary. The lowermost boundary may correspond, for example, to the spatial coordinates of a foot of the individual being monitored, to the floor of the room, and/or to the lowermost edge of detection of depth sensor 105. In some implementations, the lowermost boundary corresponds to another portion of the body, such as a halfway point to the foot or floor. The purpose of step 225 is to improve the detection rate of an assistive device by eliminating sections of the environment that could not possibly contain an actively-used assistive device. In this way, in some implementations, only the volumetric data of the region of space that lies beneath the hand and between the hand and the floor is retained for subsequent steps.

In some implementations, in step 230, further pruning of the volumetric data of step 225 takes place. For example, pixels in the depth map of step 215 that appear to be erroneous, or for which no depth value was successfully calculated, may be eliminated in step 230. For example, a pixel which appears to be "floating" by itself, isolated in space, is likely an error of noise, and may be eliminated in step 230.

In step 235, the volumetric data of steps 225 and/or 230 are evaluated for the presence of a vertical rod-like, hook-like, or mesh-like object, corresponding to the approximate shape and/or morphology of an assistive device. In some implementations, a spatial band-pass filter configured to the diameter of a standard-sized assistive device is applied to the volumetric data of steps 225 and/or 230. In some implementations, a curve-fitting algorithm corresponding to the hemispherical shape of the front of a standard-sized assistive device is applied to the volumetric data of steps 225 and/or 230 (note that the depth sensor 105 cannot view the occluded back surface of the assistive device). In some implementations, a 3D edge-detection convolution is applied to the volumetric data of steps 225 and/or 230, and the edges then evaluated for contrast with environment and degree of verticality. In some implementations, a vertical linear Hough transform filter is applied to the volumetric data of steps 225 and/or 230. In general, Step 235 employs a predetermined evaluation to assign a probability to the single frame of data from step 215 that an assistive device is present and being held vertically (and therefore employed in use) by the individual being monitored.

In some implementations, in step 240, the single-frame probability of step 235 is compared to a plurality of previous executions of step 235 for a plurality of prior frames in order to assign a probability over multiple frames of data that an assistive device is present and being held vertically (and therefore presumably in use). An example in which three frames are captured is illustrative. For illustration purposes, if a frame at time t=0 milliseconds is assigned probability of an individual using an assistive device of 40%, a frame at time t=500 milliseconds is assigned probability of the individual using an assistive device of 80%, and a frame at time t=1000 milliseconds is assigned probability of the individual using an assistive device of 50%, then the overall probability of using an assistive device during the cumulative full second of time might be assigned the average value of 57% (=(40+80+50)÷3).

In step 245, the probabilistic measurements of steps 235 and/or 240 are stored and/or transmitted for future use. For example, they may be placed into a database or sent to a remote clinician.

Step 248 decides whether to proceed to a new frame of data (for example, if the individual being monitored leaves the field-of-view, or if software execution is ended by a user) and step 249 ends the block diagram.

The system 100 may optionally contain a screen or monitor by which to display feedback of software module 115 to the individual being monitored for example, to verify correct detection of cane use, or to provide touchscreen controls. In some embodiments of system 100, there is no screen or touchscreen controls. The system 100 may optionally be housed in an enclosure 125 for ease of transport and installation. In some embodiments of system 100, there is no enclosure.

In view of the structure, functions and apparatus of the systems and methods described here, in some implementations, a system and method for measuring the frequency and duration of use of an assistive device for ambulation are provided. Having described certain implementations of methods and apparatus for integrating commercial off-the-shelf devices to produce a cost-effective, reliable, and privacy-protective detection system, it will now become apparent to one of skill in the art that other implementations incorporating the concepts of the disclosure may be used. Therefore, the disclosure should not be limited to certain implementations, but rather should be limited only by the spirit and scope of the following claims.

Throughout the description, where apparatus and systems are described as having, including, or comprising specific components, or where processes and methods are described as having, including, or comprising specific steps, it is contemplated that, additionally, there are apparatus, and systems of the disclosed technology that consist essentially of, or consist of, the recited components, and that there are processes and methods according to the disclosed technology that consist essentially of, or consist of, the recited processing steps.

It should be understood that the order of steps or order for performing certain action is immaterial so long as the disclosed technology remains operable. Moreover, two or more steps or actions may be conducted simultaneously.

What is claimed is:

1. A method of detecting an individual's use of an assistive device for mobility such that a severity of a disease and/or an individual's response to a treatment can be tracked/assessed over time, the method comprising:
   capturing, by a depth sensor, a time sequence of frames of depth data for a space, wherein the time sequence of frames comprises a plurality of frames;
   determining, by a processor of a computing device, spatial coordinates of a hand of the individual in each frame in the sequence of frames;
   determining, by the processor, volumetric data beneath the hand of the individual in each frame of the sequence of frames; and
   determining, by the processor, a plurality of probabilities of whether the individual is holding the assistive device, wherein each probability of the plurality of probabilities is a probability, for a frame of the sequence of frames, that the hand of the individual is holding an object in space consistent with the shape, size, and orientation of an assistive device for ambulation based at least in part on the volumetric data beneath the hand of the individual in the frame.

2. The method of claim 1, comprising:
   prior to determining a plurality of probabilities, pruning of the volumetric data.

3. The method of claim 1, comprising:
   determining, by the processor, a multi-frame probability that the hand of the individual is holding an object in space consistent with the shape, size, and orientation of an assistive device for ambulation based at least in part by comparing the plurality of probabilities for the sequence of frames.

4. The method of claim 1, comprising:
   providing, by an energy emitter, energy within a field-of-view for generating a depth map of the field-of-view.

5. The method of claim 1, comprising:
   determining, by the processor, a probability for a portion of the time sequence of frames that the individual is using an assistive device for ambulation over the duration of time encompassed by the portion of the sequence of frames, wherein the portions of the time sequence of frames comprises two or more frames.

6. The method of claim 5, comprising:
   storing in a database, by the processor, the plurality of probabilities such that frequencies and durations of assistive-device use are stored for the individual.

7. The method of claim 6, comprising:
   storing in a database, by the processor, at least one of the plurality of probabilities such that historic measurements are stored for the individual.

8. The method of claim 1, wherein the assistive device is a cane, crutch, rollator, or mobility walker.

9. The method of claim 1, wherein the depth sensor does not employ visible light to acquire depth data.

10. The method of claim 1, wherein a health status of the individual is monitored without acquiring visual-light images or video.

11. The method of claim 1, comprising:
   capturing, by an audio sensor, sound data for determining a decline in a health status of the individual.

12. The method of claim 1, wherein the data captured corresponding to the individual within the field-of-view is captured in real-time while the individual moves about in real-time.

13. The method of claim 1, wherein:
   energy emitted by an energy emitter comprises a pattern of emitted energy,
   energy detected by the depth sensor comprises a pattern of reflected energy, and
   the depth data for the field-of-view is generated based on a difference between the pattern of the emitted energy and the pattern of reflected energy.

14. The method of claim 1, wherein
   the depth data for the field-of-view is generated based on a difference between a phase of emitted energy and a phase of captured energy.

15. The method of claim 1, comprising:
   prior to determining spatial coordinates of the hand of the individual in each frame in the sequence of frames, extracting, by the processor, skeleton data for each frame in the sequence of frames, wherein the spatial coordinates of the hand of the individual in each frame in the time sequence of frames are determined based at least in part on the skeleton data for the respective frame.

16. A system of detecting an individual's use of an assistive device for mobility such that a severity of a disease and/or an individual's response to a treatment can be tracked/assessed over time, the system comprising:

at least one energy emitter for emitting energy within a field of view for generating a depth map of the field-of-view;

at least one depth sensor for capturing energy reflected from one or more objects positioned within the field of view, wherein the one or more objects comprises the individual; and a computing device comprising a processor and a memory storing instructions thereon, that when executed by the processor, cause the processor to:

determine spatial coordinates of a hand of the individual in each frame in the sequence of frames;

determine volumetric data beneath the hand of the individual in each frame of the sequence of frames; and determine a plurality of probabilities of whether the individual is holding the assistive device, wherein each probability of the plurality of probabilities is a probability, for a frame of the sequence of frames, that the hand of the individual is holding an object in space consistent with the shape, size, and orientation of an assistive device for ambulation based at least in part on the volumetric data beneath the hand of the individual in the frame.

17. The system of claim 16, wherein the instructions stored on the memory comprise instructions that, when executed by the processor, cause the processor to:

prior to determining a plurality of probabilities, prune the volumetric data.

18. The system of claim 16, wherein the instructions stored on the memory comprise instructions that, when executed by the processor, cause the processor to:

determine a multi-frame probability that the hand of the individual is holding an object in space consistent with the shape, size, and orientation of an assistive device for ambulation based at least in part by comparing the plurality of probabilities for the sequence of frames.

19. The system of claim 16, wherein the instructions stored on the memory comprise instructions that, when executed by the processor, cause the processor to:

determine a probability for a portion of the time sequence of frames that the individual is using an assistive device for ambulation over the duration of time encompassed by the portion of the sequence of frames, wherein the portions of the time sequence of frames comprises two or more frames.

20. The system of claim 16, wherein the instructions stored on the memory comprise instructions that, when executed by the processor, cause the processor to: prior to determining spatial coordinates of the hand of the individual in each frame in the sequence of frames, extract skeleton data for each frame in the sequence of frames, wherein the spatial coordinates of the hand of the individual in each frame in the time sequence of frames are determined based at least in part on the skeleton data for the respective frame.

* * * * *